United States Patent
Bonitz

[11] Patent Number: 5,708,208
[45] Date of Patent: Jan. 13, 1998

[54] TESTING HEAD FOR THE ULTRASONIC TESTING OF A BUILT-IN POLYGONAL SOCKET SCREW

[75] Inventor: Frank Bonitz, Neunkirchen, Germany

[73] Assignee: ABB Reaktor GmbH, Mannheim, Germany

[21] Appl. No.: 616,218

[22] Filed: Mar. 15, 1996

[30] Foreign Application Priority Data

Mar. 15, 1995 [DE] Germany ............. 195 09 290.2

[51] Int. Cl.$^6$ ............................................. G01N 29/24
[52] U.S. Cl. ......................... 73/644; 73/598; 73/628
[58] Field of Search ..................... 73/644, 632, 660, 73/598, 628, 629, DIG. 1; 340/680, 683

[56] References Cited

U.S. PATENT DOCUMENTS

| | | |
|---|---|---|
| 4,020,679 | 5/1977 | Barry . |
| 4,062,227 | 12/1977 | Heyman .................. 73/630 |
| 4,603,701 | 8/1986 | Chen ....................... 73/644 |
| 4,640,131 | 2/1987 | Kroning ................... 73/644 |
| 4,796,632 | 1/1989 | Boyd ....................... 73/644 |
| 5,095,753 | 3/1992 | Russ ........................ 73/598 |
| 5,156,050 | 10/1992 | Schmid .................... 73/644 |
| 5,531,119 | 7/1996 | Meyers .................... 73/644 |

FOREIGN PATENT DOCUMENTS

| | | |
|---|---|---|
| 22 04 237 | 9/1972 | Germany . |
| 94/27143 | 11/1994 | WIPO . |

OTHER PUBLICATIONS

"Ultrasonic Testing of Materials" (Krautkrämer et al.), Siemens AG,ZFE FID 2, 4th revised edition, pp. 266–268. 1990 (no month).

Primary Examiner—Christine K. Oda
Attorney, Agent, or Firm—Herbert L. Lerner; Laurence A. Greenberg

[57] ABSTRACT

A testing head is provided which operates in accordance with the contact technique and has a flexibly constructed adaptor piece that is adapted to an intended contour of the conical bottom surface. A ring structure, which is disposed on the base surface of the adaptor piece, is constructed as a one-piece or multiple-piece ultrasonic transducer.

5 Claims, 2 Drawing Sheets

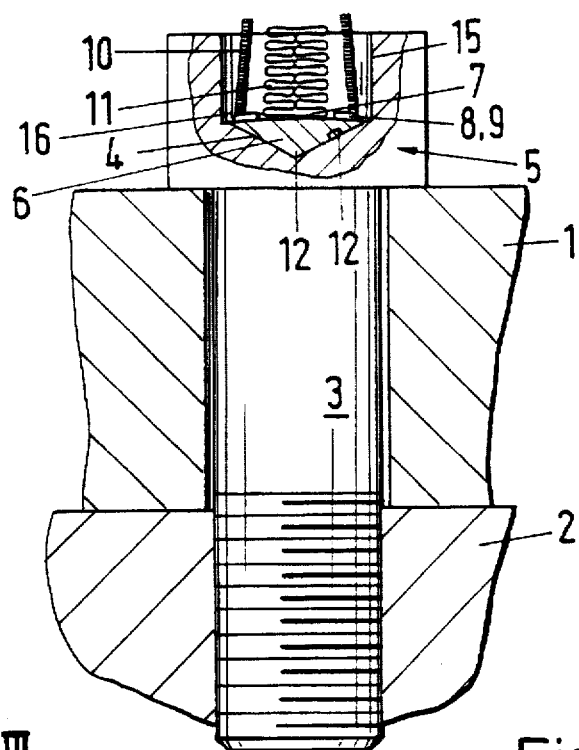
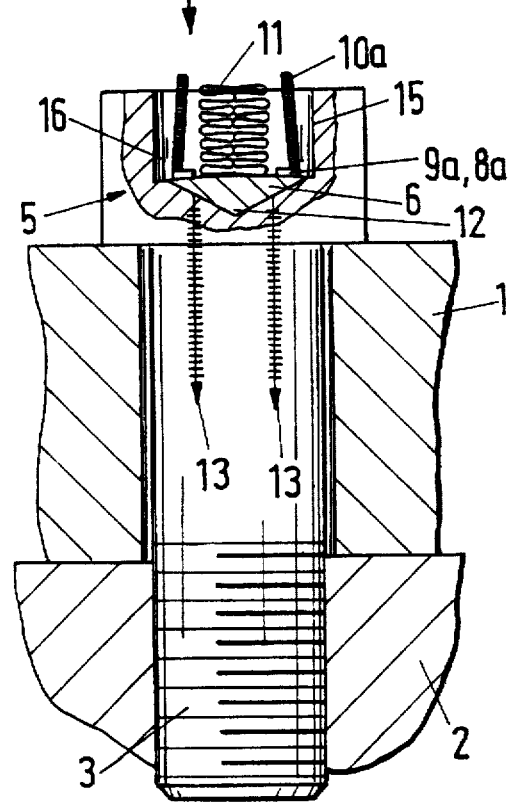
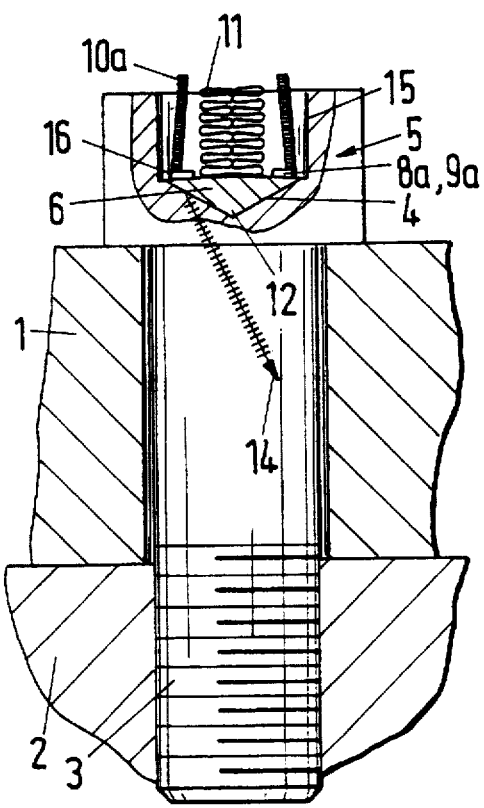

TESTING HEAD FOR THE ULTRASONIC TESTING OF A BUILT-IN POLYGONAL SOCKET SCREW

BACKGROUND OF THE INVENTION

Field of the Invention

The invention relates to a testing head for the ultrasonic testing of a built-in polygonal socket screw having a polygonal socket with an adjoining bottom surface, the testing head includes an accommodation part for at least one ultrasonic transducer disposed on a side of the accommodation part facing away from the bottom surface, and the accommodation part is an adaptor piece having an intended contour of the bottom surface.

Such a testing head is disclosed by U.S. Pat. No. 5,156,055. In that device the contour of the bottom surface of the hexagonal socket exhibits production tolerances. The coupling body, which is formed of a solid material, cannot compensate for those production tolerances, so that a contact covering the entire surface between the coupling body and the bottom surface is not provided. Imprecise measurement results are the consequence. Furthermore, the guidance of the testing head is prescribed by a centering between a housing of the testing head and an outer surface of the hexagonal socket. Unavoidable production tolerances also lead in this case to faulty contact of the coupling body on the bottom surface, which is, for example, of conical construction, if the centering between the outer surface and the housing no longer allows centering between the coupling body and the bottom surface.

U.S. Pat. No. 3,921,442 discloses a coupling element for an ultrasonic testing device, the material of which has an affinity for water and therefore behaves acoustically somewhat like water. The material being used can also be elastic.

According to Published European Patent Application 0 635 719 A2, a known, boot-like ultrasonic transducer, which is moved along a welded seam or on another rough specimen surface, has a liquid filling which is enclosed by a flexible membrane.

Furthermore, German Published, Non-Prosecuted Application DE 35 04 522 A1 discloses an ultrasonic testing device for a slotted screw. In that case, an ultrasonic testing head is placed on each end portion of the screw which is bounded by a slot.

Finally, German Patent DE 40 05 545 C2 discloses a testing configuration for headed screws which are accessible from the end. The construction of the ultrasonic testing head is not mentioned there. It can be seen, in particular from FIG. 2 of German Patent DE 40 05 545 C2, that, because of the distance between the end of the screw and the ultrasonic transducers, testing is clearly carried out in accordance with the immersion technique. The ensonification, using vertical testing heads which are constructed for the immersion technique application, that apply the ultrasound through a pilot water path, is sensitive to inaccuracies in the positioning of the testing head and its alignment. Those inaccuracies, in the case of testing by the immersion technique, lead to deformation of the sound field and thus to restrictions on the sensor configuration for the testing task. In particular, testing by the immersion technique is sensitive to the tolerances in the configuration of the bottom surface of the polygonal socket, if the latter is implemented as a bored conical surface.

SUMMARY OF THE INVENTION

It is accordingly an object of the invention to provide a testing head for the ultrasonic testing of a built-in polygonal socket screw, which overcomes the hereinafore-mentioned disadvantages of the heretofore-known devices of this general type and which makes possible testing accessible through a bottom surface of the polygonal socket while overcoming inaccuracies.

With the foregoing and other objects in view there is provided, in accordance with the invention, a testing head for the ultrasonic testing of a built-in polygonal socket screw having a polygonal socket with a bottom surface and an outer surface, the testing head comprising an accommodation part having a side facing away from the bottom surface, the accommodation part being an adaptor piece formed of a flexible material with an intended contour of the bottom surface, the adaptor piece having a periphery spaced apart from the outer surface of the polygonal socket defining a free space therebetween; and at least one ultrasonic transducer being constructed as a ring and being disposed on the side of the accommodation part facing away from the bottom surface.

The adaptor piece compensates for tolerances in the bottom surface in relation to the intended contour. The homogeneous annular structure of the ultrasonic transducer ensures that the sought-after sound direction can be maintained by tracing the flexible adaptation movement of the adaptor piece, as a result of which a constant testing sensitivity of the ultrasonic transducer is achieved. The free space results in centering of the testing head being carried out merely between the adaptor piece and the bottom surface.

In accordance with another feature of the invention, for the purpose of damping undesired propagation of sound, the side of the adaptor piece which faces the bottom surface is partly constructed to be sound-absorbing.

In accordance with a further feature of the invention, the side of the adaptor piece which faces away from the bottom surface of the polygonal socket is constructed as a flat or conical base surface.

Therefore, the shape of the base surface is simultaneously used for forming a specific angle of incidence of sound.

In accordance with a concomitant feature of the invention, the ring is a ring structure composed of individual ultrasonic transducers, wherein it is possible to take into operation all of the ultrasonic transducers together, a group of ultrasonic transducers or an individual ultrasonic transducer.

A variable sound field structure can thus be generated in a test object. In this case, partial regions in the screw can be tested with increased sensitivity. As a result of corresponding cycling through individual ultrasonic transducers or ultrasonic transducers connected together to form groups, it is possible to control the sensitivity of the testing head as well as the spatial position of the sensitivity zone. As a result of the operation of various individual ultrasonic transducers or groups of ultrasonic transducers for the transmitting mode and the receiving mode, it is possible for the ultrasonic waves to be incident at an angle to the axial axis of the screw. During operation of the entire configuration, on the other hand, a sound field having emission in the axial direction can be achieved by overlaying all of the emitted sound waves from the individual ultrasonic transducers. During the operation of the individual ultrasonic transducers as a whole or during the operation of individual subassemblies, it is possible to control the directional effect and focusing property of the transmitting and receiving configuration in a deliberate manner through the use of suitable line delays of the transmitting excitation or of transmission time delays of the received signals of the individual elements.

Other features which are considered as characteristic for the invention are set forth in the appended claims.

Although the invention is illustrated and described herein as embodied in a testing head for the ultrasonic testing of a built-in polygonal socket screw, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a fragmentary, diagrammatic, partly broken-away, longitudinal-sectional view of a polygonal socket screw being inserted into a component, with an ultrasonic testing head;

FIG. 2 is a view similar to FIG. 1 showing an ultrasonic testing head during an ensonification process;

FIG. 3 is another view similar to FIG. 1 showing an ultrasonic testing head during another ensonification process;

DESCRIPTION OF THE PREFERRED EMBODIMENTS

Figure 4:
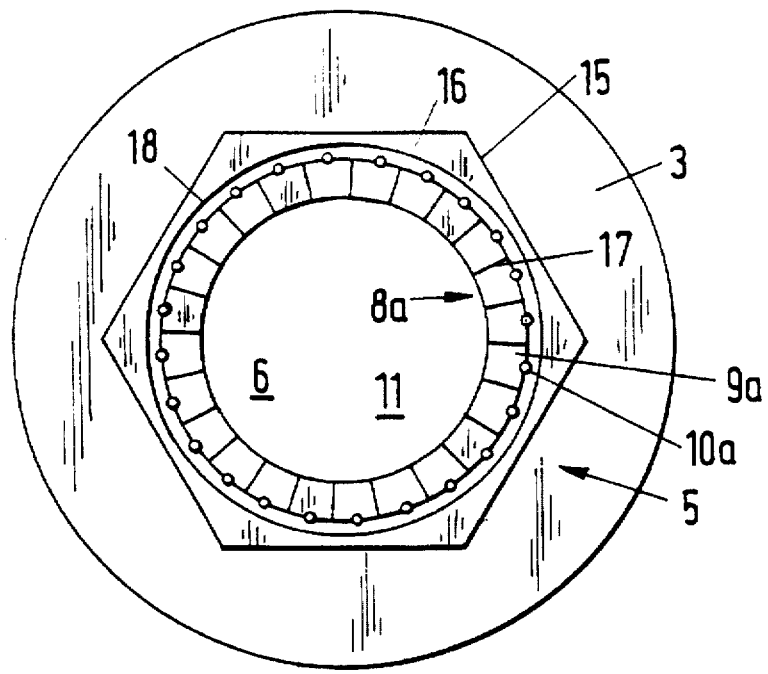
FIG. 4 is an enlarged top-plan view of the screw and a testing head, which is taken in a direction of an arrow III of FIG. 2 or FIG. 3.

Referring now to the figures of the drawings in detail and first, particularly, to FIGS. 1–3 thereof, there is seen a longitudinal section through two components 1, 2 which are connected to each other through a polygonal socket screw 3.

A bottom surface 4 which is adjoined by a polygonal socket 15, is of conical construction and represents a so-called bored cone. An ultrasonic testing head 5 is moved into a position shown in FIGS. 1 to 3 for the purpose of testing the screw 3, in particular a shank of the screw and a transition region between the screw shank and a screw head, from the bottom surface 4.

Figure 5:
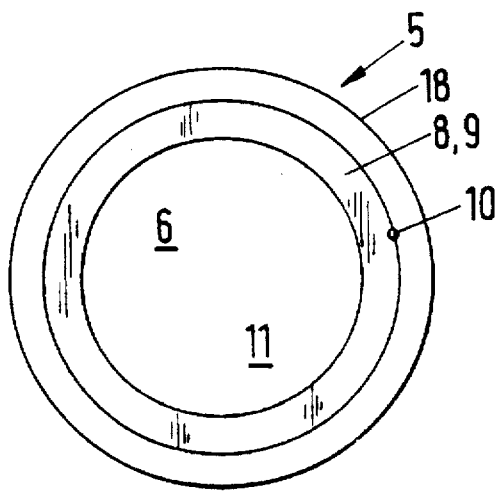
FIG. 5 is a top-pan view of a testing head according to FIG. 4 with a one-piece ring according to FIG. 1.
Figure 6:
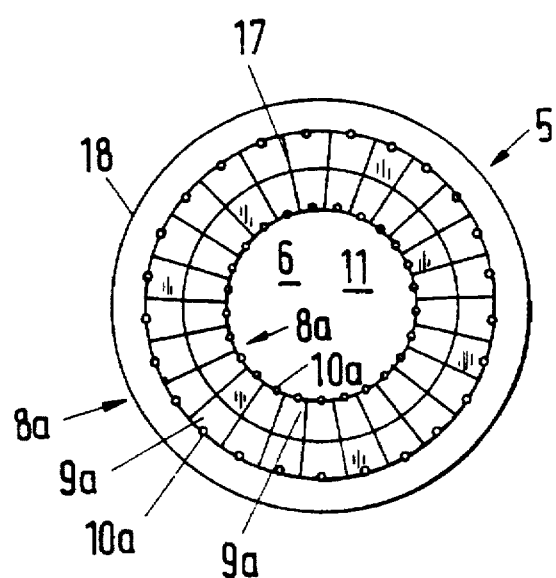
FIG. 6 is a top-plan view of a testing head according to FIG. 4 with a plurality of ring structures.

The ultrasonic testing head 5, which is seen on a larger scale in FIGS. 4, 5 and 6, has an accommodation part in the form of an adaptor piece 6 which is formed of an elastic material with low damping in an operating frequency range of the ultrasound. The adaptor piece 6 has a side facing the screw head with a shape that corresponds to an intended contour of the bottom surface 4. The adaptor piece 6 has a base surface 7 facing the bottom surface 4 which is constructed increasing slightly conically in the case of the exemplary embodiment. However, it can also be aligned flat, as seen in the horizontal direction.

A one-piece ring 8 is disposed on the base surface 7 of the adaptor piece 6 and forms a one-piece ultrasonic transducer 9 that can be seen from FIG. 5. The base surface 7 faces away from the bottom surface and is constructed as a bored cone. The ring 8 is connected to the adaptor piece 6 in such a way that it can execute any movements in adaptation to the actual contour of the bottom surface 4. A more or less severely conically constructed base surface 7 of the adaptor piece 6 influences the ensonification direction. A free space 16 is formed between an outer surface of the polygonal socket 15 and a periphery 18 of the adaptor piece 6. A spacing, which is produced as a result between the adaptor piece 6 and the outer surface of the polygonal socket 15, ensures that the centering process which is necessary for complete contact between the adaptor piece 6 and the conical region of the bottom surface 4, is not impeded. There is also a spacing between a bellows 11 serving as a holder for the adaptor piece 6 and the outer surface of the polygonal socket 15. Therefore, the centering of just the ultrasonic testing head 5 can be carried out without interference through the flexibly constructed adaptor piece 6. Supply lines and drain lines 10 lead from the ultrasonic transducer 9 to non-illustrated control and evaluation devices. The bellows 11, which are articulated in the center of the base surface 7, belong to a non-illustrated device for moving the testing head 5 relative to the screw head. An outer diameter of the ring 8 is smaller than or at most equal to the periphery 18 of the adaptor piece 6.

The adaptor piece 6 is preferably provided with inserts 12 made of sound-absorbing material, in the vicinity of its tip and/or on the conical region adjoining the base surface 7. Damping of undesired sound waves which could otherwise lead to falsification of the test result, can be achieved with the inserts.

FIGS. 2 and 3, in conjunction with FIG. 4, show a ring structure 8a which is disposed on the base surface 7 and is formed, segment-like, of a plurality of ultrasonic transducers 9a. Disposed between the ultrasonic transducers is a damping layer 17. The individual ultrasonic transducers 9a, including the damping layers 17, are connected to form the rigid ring structure 8a which simultaneously executes the necessary movements as a whole during the centering and adaptation process between the bottom surface 4 and the adaptor piece 6. Each ultrasonic transducer 9a is assigned a supply and drain line 10a leading to control and evaluation devices, which are not shown. A sound field structure prescribed by the base surface can be altered by using this configuration. The type of the respective variables depends on whether, for example, all of the ultrasonic transducers 9a are in operation at the same time or a group of ultrasonic transducers is in operation. According to the diagrammatic representation of FIG. 2, all of the ultrasonic transducers 9a are simultaneously in operation, with the result that a sound field symbolized by arrows 13 is achieved and has an emission in the axial direction of the polygonal socket screw 3. If it is intended to generate a sound field extending obliquely with respect to the screw axis, as is indicated by an arrow direction 14 according to FIG. 3, which represents a variant of the sound direction prescribed through the use of the base surface 7, the ultrasonic transducers 9a of an ultrasonic transducer group are excited in succession. Therefore, through the use of the configuration and a suitable control device, the directional effect and focusing property of the emitted and received signals can be controlled in a deliberate manner. FIG. 4 also shows the free space 16 between the periphery of the adaptor piece and the outer surface of the polygonal socket 15.

According to the construction shown in FIG. 6, two ring structures 8a are disposed concentrically with respect to each other. These ring structures may be constructed, with respect to the ultrasonic transducers 9a, in the same way as described in conjunction with FIGS. 2 to 5. This construction, which is envisaged for achieving a fine-structured test result, can also have ring structures which are not disposed concentrically with respect to one another.

I claim:

1. A testing head for the ultrasonic testing of a built-in polygonal socket screw having a polygonal socket with a bottom surface and an outer surface, the testing head comprising:

an accommodation part having a side facing away from the bottom surface, said accommodation part being an adaptor piece formed of a flexible material with an intended contour of the bottom surface, said adaptor piece having a periphery spaced apart from the outer surface of the polygonal socket defining a free space therebetween; and at least one ultrasonic transducer being constructed as a continuous ring and being disposed on said side of said accommodation part facing away from the bottom surface.

2. The testing head according to claim 1, wherein said adaptor piece has a side facing said bottom surface and being partly constructed to be sound-absorbing.

3. The testing head according to claim 1, wherein said side of said adaptor piece facing away from the bottom surface of the polygonal socket is a planar base surface.

4. The testing head according to claim 1, wherein said side of said adaptor piece facing away from the bottom surface of the polygonal socket is a conical base surface.

5. The testing head according to claim 1, wherein said ring is a ring structure formed of individual ultrasonic transducers, and said ultrasonic transducers are selectively operable all together, as a group or individually.

* * * * *